United States Patent [19]

Badylak et al.

[11] Patent Number: 5,007,927
[45] Date of Patent: Apr. 16, 1991

[54] MUSCLE-POWERED CARDIAC ASSIST DEVICE

[75] Inventors: Stephen F. Badylak; Leslie A. Geddes, both of West Lafayette, Ind.; Jerry L. Wessale, Lindenhurst, Ill.

[73] Assignee: Purdue Research Foundation, West Lafayette, Ind.

[21] Appl. No.: 426,301

[22] Filed: Oct. 24, 1989

[51] Int. Cl.$^5$ .............................................. A61F 2/16
[52] U.S. Cl. ........................................... 623/3; 600/16
[58] Field of Search ................... 623/3; 600/16, 17, 18

[56] References Cited

U.S. PATENT DOCUMENTS

| 4,666,443 | 5/1987 | Portner | 623/3 |
| 4,756,302 | 7/1988 | Portner et al. | 623/3 |
| 4,759,760 | 7/1988 | Snapp, Jr. | 623/3 |
| 4,813,952 | 3/1989 | Khalafalla | 623/3 |

Primary Examiner—Randy Citrin Shay
Attorney, Agent, or Firm—Barnes & Thornburg

[57] ABSTRACT

A method and apparatus is provided for enhancing blood circulation, and thereby reducing fatigue, in a skeletal muscle used for powering a cardiac assist device wherein the muscle is positioned to compress a blood reservoir in response to muscle contracting stimuli. Enhanced perfusion of the skeletal muscle is achieved by delaying blood flow into the reservoir for a period of time following each muscle contraction.

8 Claims, 6 Drawing Sheets

MUSCLE-POWERED CARDIAC ASSIST DEVICE

FIELD OF THE INVENTION

This invention relates to skeletal muscle powered cardiac assist devices that supplement the pumping action of a failing heart. More particularly, the invention is directed to increasing blood circulation and concommitantly minimizing fatigue in skeletal muscle used in such devices.

BACKGROUND AND SUMMARY OF THE INVENTION

Medical practitioners have acknowledged a great need for implantable cardiac assist devices for supplementing the blood pumping action of a diseased or failing heart. It has been estimated that over 400,000 people in the United States could benefit from permanently implantable cardiac assist devices. Such devices not only work to alleviate bodily dysfunctions attributable to reduced blood pumping ability of the failing heart, but they can also promote the healing of the diseased or failing heart by reducing its required contractile load and can protect other organs from failure due to poor circulation.

One cardiac assist device known in the art is the left ventricular assist pump. That device consists of a pump with a pumping chamber connected via a blood inlet to the left ventricle of a failing heart and via a blood outlet to the aorta. In operation, the pumping chamber fills with blood in response to blood pressure from a natural contraction of the left ventricle. After the pump chamber is filled and the heart is in diastole, the blood inlet is closed by a unidirectional pressure controlled valve that blocks the flow of blood from the pumping chamber back through the inlet into the left ventricle of the failing heart. Subsequent to closure of the valve, the pumping chamber is compressed by the action of a power source. The blood contained in the pumping chamber is ejected from the pumping chamber through the outlet valve into the aorta, thereby supplementing the pumping action of the failing heart. The pumping action is coordinated with natural heart function with the aid of sensors positioned to monitor electrical activity of the heart.

The widespread use of the ventricular assist pump or similar types of cardiac assist devices has been greatly limited by the lack of suitable power sources. Under normal physiologic conditions for adults at rest, about 3 to about 5 watts of power are required to pump blood. Even though cardiac assist devices only supplement and do not completely replace the pumping action of the heart, it is important that they reliably deliver substantial power for periods of years without recharging, replacement or maintenance. One proposed power source that has many of these features is skeletal muscle. The contractile force produced by electrically stimulated autogenous skeletal muscle can be used to power an implanted blood pump.

As disclosed in U.S. Pat. No. 4,813,952, issued Mar. 21, 1989, to Khalafalla, expressly incorporated herein by reference, the use of autogenous skeletal muscle to power a cardiac assist blood pump is known in the art. Commonly employed skeletal muscles include the rectus abdominis, the latissimus dorsi, or other muscles that can be translocated from their normal positions with their associated neurovascular supply left intact, and wrapped around a blood reservoir, typically a flexible pouch, having blood conduits connecting it to the circulatory system. Blood pumping action of such cardiac assist devices is powered by the contractile forces exerted bY the innervated skeletal muscle in response to electrical stimulation of the appropriate skeletal muscle nerves. In operation, the flexible pouch fills with blood from the circulatory system, stretching the skeletal muscles wrapped around the pouch. Timed electrical pulses produced by a pulse generator trigger the contraction of the skeletal muscle. The timing of the electrical pulses is typically coordinated with sensed natural heart activity. As the flexible pouch is compressed by the contracting skeletal muscle, the blood contained in the pouch is pumped into the aorta or other major artery of the patient's circulatory system, thereby supplementing the natural blood pumping action of the heart.

The overall function and efficiency of such cardiac assist devices depends on a number of factors including the configuration of the flexible pouch or blood reservoir and its connection to the circulatory system, the identity and condition of the muscle used to wrap the flexible pouch, amplitude, frequency and duration of the electrical pulses used to trigger muscle contraction, and coordination of pumping action with the natural pumping action of the heart. With optimization of such variables cardiac assist devices have been able to deliver as much as 20% to 80% of the pumping activity of a normal heart, but only for brief periods of time. Skeletal muscle fatigues rapidly when it is required to contract rhythymically at rates matching the normal heart contraction rate. Because the volume of blood pumped by this type of cardiac assist device rapidly diminishes as the skeletal muscle becomes fatigued, clinical use of skeletal muscle powered cardiac assist devices has been limited.

It is therefore an object of this invention to provide a method for minimizing fatigue in skeletal muscles used to power cardiac assist pumps.

It is another object of this invention to provide an apparatus for minimizing fatigue in skeletal muscle in use for powering a cardiac assist device having a blood reservoir and a skeletal muscle positioned to compress the blood reservoir in response to a muscle contracting stimulus.

Still another object of this invention is to provide a method and apparatus for increasing blood circulation in skeletal muscle in use for powering cardiac assist devices.

In accordance with the foregoing objectives, there is provided an apparatus for enhancing circulation of blood through skeletal muscle in use for powering a cardiac assist device designed to provide blood pumping action to supplement the pumping action of a diseased or failing heart. The device includes a blood reservoir in fluid communication with a patient's circulatory system. The skeletal muscle used for powering the cardiac assist device is positioned to compress the blood reservoir in response to a muscle contracting stimulus typically produced by a pulse generator programmed to initiate the signal in a predetermined time relationship to sensed heart function. Blood circulation within the skeletal muscle is enhanced by use of a valve positioned to control blood flow from the patient's circulatory system into the blood reservoir. The valve is opened and closed in a timed relationship to the skeletal muscle contracting stimulus and/or heart activity. More particularly, the valve is controlled to close immediately before and for a predetermined, but preferably programmable, time period following contraction of the skeletal muscle.

Without the use of the valve to block flow of blood from the patient's circulatory system into the blood reservoir for a period of time following each muscle contraction, blood would immediately begin filling the blood reservoir following muscle contraction. The pressure exerted by the blood reservoir against the skeletal muscle as the reservoir fills with blood is sufficient to compress the arterioles and other small blood vessels distributed through the skeletal muscle, thereby diminishing blood flow and the transport of oxygen and other needed nutriments to, and transport of waste products from, skeletal muscle cells. This diminished transport results in muscle fatigue. Delaying the flow of blood into the blood reservoir for a predetermined length of time after each muscle contraction lengthens the time between muscle contractions during which blood can circulate in the skeletal muscle. This enhanced blood circulation has been found to greatly reduce fatigue of the muscle. More time is allowed for delivery of necessary nutriments to skeletal muscle cells, and removal of waste products. The consequent reduction in skeletal muscle fatigue enables continuous use of skeletal muscle powered cardiac assist devices at contraction rates approaching the heart contraction rate with a long term, sustained blood pumping capacity.

In a preferred embodiment, skeletal muscle such as a rectus abdominis along with its associated neurovascular system is translocated from its normal position in a patient's body and wrapped around a blood reservoir, typically a flexible pouch. The flexible pouch is in fluid communication with the patient's circulatory system through a blood outlet conduit and a blood inlet conduit. The blood outlet conduit includes a unidirectional valve placed to prevent blood flow from the patient's circulatory system into the blood reservoir. A valve is positioned to control blood flow into the blood reservoir from the patient's circulatory system through the blood inlet conduit. In a most preferred embodiment, the valve is biased to remain in a closed position until activated. The valve can be activated to the opened position by a signal from a pulse generator. The valve is opened and closed during operation of the cardiac assist device in a timed relationship to the muscle contracting stimulus.

Thus, prior to each skeletal muscle contraction, and optionally in coordination with heart activity, the valve is opened for a controlled period of time (the valve open time) to allow blood to flow from a patient's circulatory system into the flexible pouch. Blood flowing into the flexible pouch causes it to expand, thereby applying pressure to and stretching the skeletal muscle wrapped around the pouch. Controlling the amount of blood flowing from the patient's circulatory system into the flexible pouch (by controlling the valve open time) allows selection of the desired precontraction pressure exerted by the flexible pouch against the skeletal muscle. Increasing the precontraction pressure on the skeletal muscle, up to a limit, acts to increase the available contractile force that can be exerted by the skeletal muscle. The valve is closed to block blood flow in the blood inlet conduit prior to application of a muscle contracting stimulus to the skeletal muscle. Contraction of the skeletal muscle in response to the muscle contracting stimulus forces the blood contained in the flexible pouch through the blood outlet conduit into the patient's circulatory system. Repetition of this sequence supplements the blood pumping action of the circulatory system of a patient's body. Optionally, the muscle contracting stimulus can be applied to the skeletal muscle in coordination with the pumping action of the heart, as sensed by a heart sensor suitably positioned to monitor heart activity.

Fatigue of skeletal muscle in use for powering a cardiac assist device having a valve to control the flow of blood into the blood reservoir can also be reduced by applying to the muscle a training regimen in the form of an electrical stimulus to promote conversion of fast twitch muscle fibers into slow twitch muscle fibers. Slow twitch muscle fiber has a greater tolerance for long term contractile loading than does fast twitch muscle fiber. Since about 50% of a typical skeletal muscle is composed of the easily fatigued fast twitch muscle fiber, skeletal muscle fatigue in cardiac assist devices can be reduced with conversion of fast twitch muscle fibers into slow twitch muscle fibers. That conversion can be promoted by a muscle training regimen that includes applying to the skeletal muscle an electrical stimulus having a predetermined amplitude, frequency, and duration. The preferred training regimen includes the application of series of electrical pulses to cause muscle twitching, alternated with a train of optionally ramped electrical pulses to cause a smooth tetanic muscle contraction. Conversion of fast twitch muscle fibers into less easily fatigued slow twitch muscle fibers is essentially complete after a six week training regimen. The training regimen permits cardiac assist function during the training period. Such muscle training can therefore be done "on the job", after implantation of the cardiac assist device and during its operation.

The present invention enables implantation of skeletal muscle powered cardiac assist devices for long term operation. Previous devices of that type were limited because of power considerations and muscle fatigue. The present method and apparatus allows enhanced perfusion of the skeletal muscle to reduce muscle fatigue by delaying the flow of blood into a blood reservoir for a predetermined time following each muscle contracting stimulus applied to skeletal muscle positioned to compress the blood reservoir.

The present invention is readily adapted to art recognized cardiac assist devices that use skeletal muscle power. Valves that can be controlled to block or permit flow of blood through a blood inlet into a blood reservoir are commercially available. Such a valve can be used for example, to replace the unidirectional valve in the blood inlet conduit of the cardiac assist device described in U.S. Pat. No. 4,813,952. Further, programmable heart sensor/pulse generators are available and readily adapted for use in accordance with this invention.

Additional objects, features, and advantages of the invention will become apparent to those skilled in the art on consideration of the following detailed description of preferred embodiments.

DETAILED DESCRIPTION OF THE DRAWINGS

Figure 1:
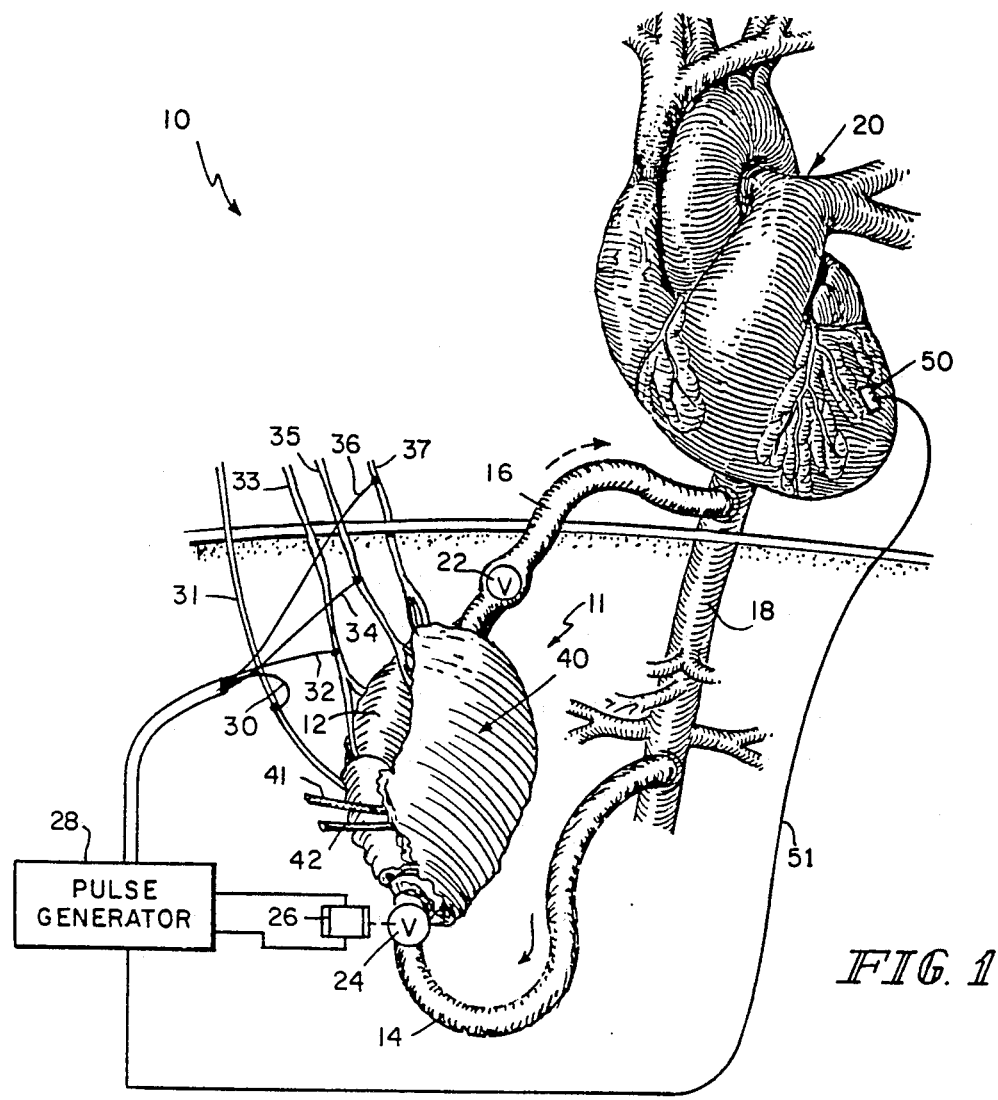
FIG. 1 is a schematic representation of a skeletal muscle powered cardiac assist device utilizing the present apparatus.

With reference to FIG. 1, cardiac assist device 10 is implanted in a patient's body to supplement the blood pumping action of diseased or failing heart 20. In this embodiment the assist device is connected between two points along the aorta. Cardiac assist device 10 has a skeletal muscle ventricle 11 that includes a flexible pouch 12 and a rectus abdominis muscle 40, a blood inlet conduit 14 and a blood outlet conduit 16, are connected between the skeletal muscle ventricle 11 and aorta 18. Flexible pouch 12 and conduits 14, 16 can be constructed with a tissue graft material such as that described in copending U.S. application now U.S. Pat. No. 4,902,508 issued Feb. 20, 1990 Ser. No. 07/217,299 filed July 11, 1986, a biocompatible polymer such as polyethylene, or processed collagen that can withstand repeated flexure and compression/expansion cycles for the expected lifetime of cardiac assist device 10.

The rectus abdominis muscle 40 having associated motor nerves 31, 33, 35, and 37 is translocated from its normal position, then wrapped around flexible pouch 12, and sutured in place. A superior epigastric artery 41 and a superior epigastric vein 42 are the major circulatory vessels supplying and removing blood from the rectus abdominis muscle 40. Motor nerves 31, 33, 35, and 37 are connected to electrical leads 30, 32, 34, and 36 respectively. Leads 30, 32, 34, and 36 are in electrical communication with a pulse generator 28. Pulse generator 28 receives electrical signals indicative of heart function from heart sensor 50 through sensor lead 51 and generates a series of electrical pulses (skeletal muscle contracting stimuli) that stimulate contraction of the rectus abdominis 40 in timed relationship with the sensed activity of heart 20.

Pulse generator 28 also controls an electrically activated valve 24 placed in blood inlet conduit 14. Valve 24 is biased in the closed position and is opened by solenoid 26 in response to electrical activation signals from pulse generator 28. When opened by the solenoid 26, the valve 24 permits blood flow from aorta 18 into the flexible pouch 12.

Unidirectional valve 22 is located in blood outlet conduit 16. In one embodiment, unidirectional blood outlet valve 22 is a pressure actuated flap valve. As illustrated, blood outlet valve 22 permits blood flow only toward aorta 18.

Figure 7:
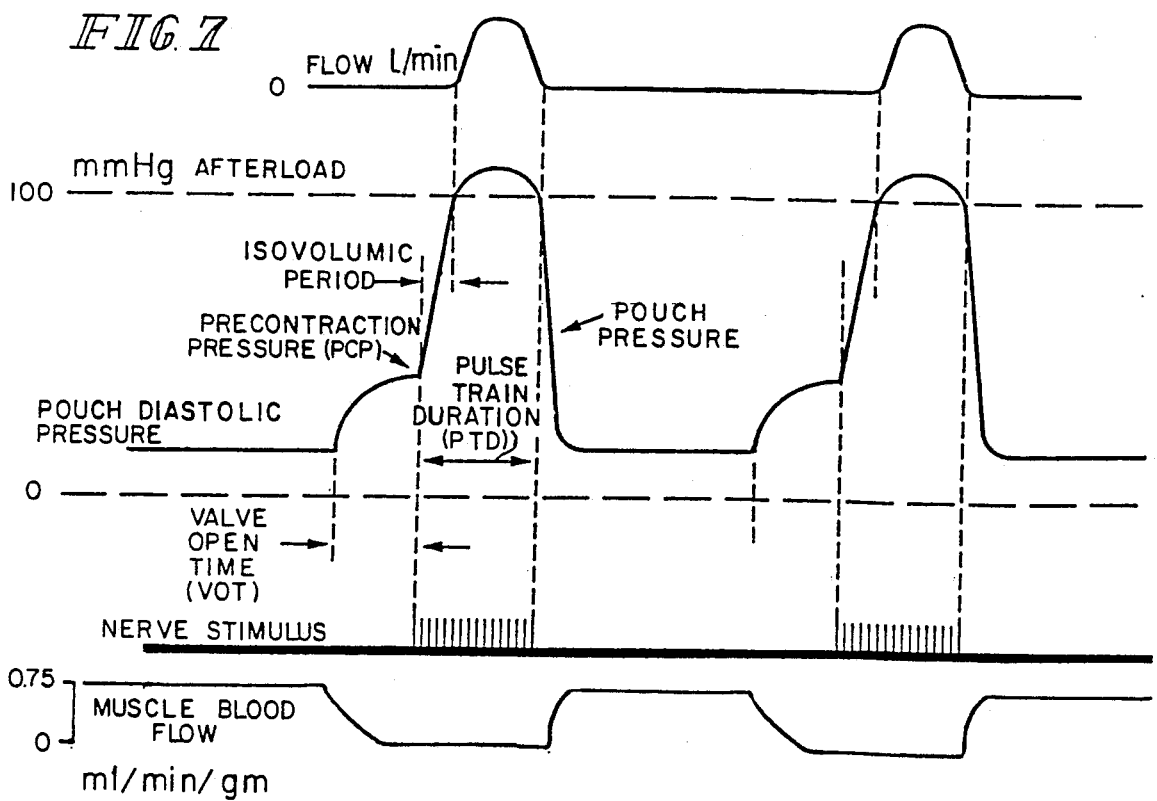
FIG. 7 is a timing diagram showing output flow from the flexible pouch (L/min), pressure in the pouch (mmHg), the train of muscle contracting stimuli, and muscle capillary blood flow (mL/min)

Operation of cardiac assist device 10 shown in FIG. 1 is best articulated with reference to FIG. 7. Each cycle of its operation generally can be divided into three sequential phases: (1) a skeletal muscle perfusion phase with valve 24 closed, immediately following termination of the skeletal muscle contracting stimulus, and during which phase blood perfuses capillaries (not shown) of muscle 40; (2) a pouch filling phase initiated by opening of valve 24 and ending with the closing of valve 24 during which phase the flexible pouch 12 fills with blood, simultaneously stretching muscle 40 surrounding the flexible pouch 12 and restricting perfusion of muscle 40; and (3) a muscle contraction phase, with valve 24 closed and pulse generator 28 providing the muscle contracting stimulus through leads 30, 32, 34, 36 to muscle 40, during which the blood contained in flexible pouch 12 is expelled from flexible pouch 12 through blood outlet conduit 16 and valve 22 into aorta 18 by the compressive forces exerted by contracting rectus abdominis muscle 40.

The operational cycle illustrated in FIG. 7 begins at the skeletal muscle perfusion phase with flexible pouch 12 in a collapsed state and having a low pouch pressure of about 5-15 millimeters of Hg. Because both valve 24 and valve 22 are closed during this phase, the flow of blood through muscle 40 reaches a high of typically about 0.75 ml/min/gm of muscle. Nutriments are delivered to muscle cells and metabolic wastes are removed by blood perfusing the muscle tissue.

Figure 2:
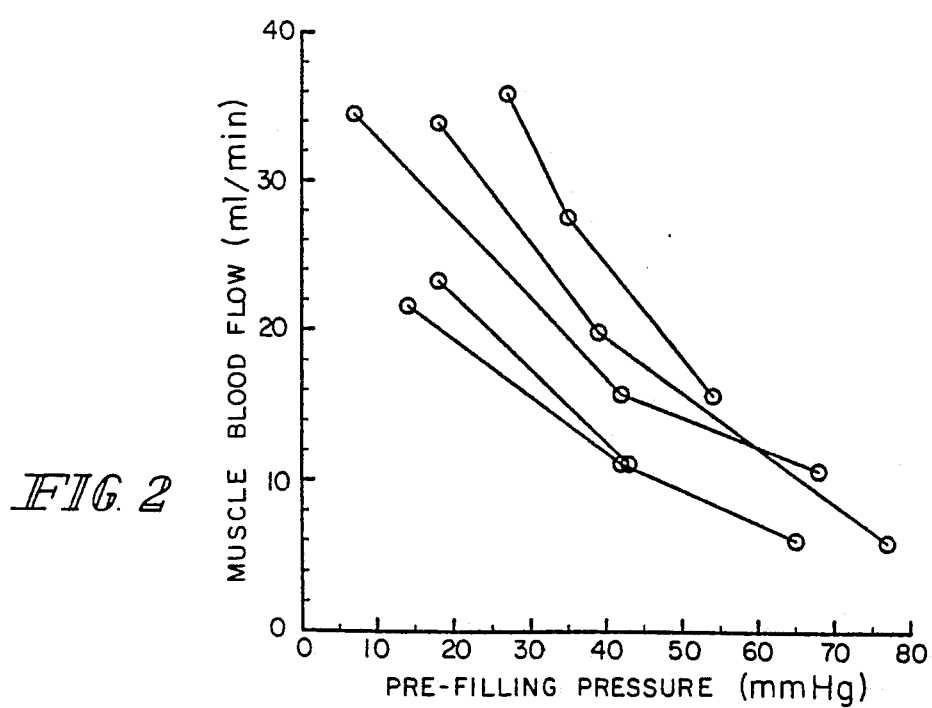
FIG. 2 is a graphic representation of the reduction in skeletal muscle blood capillary flow with increasing flexible pouch pressure in a device similar to that shown in FIG. 1.

FIG. 2 is a graph showing the dependence of blood flow through skeletal muscle wrapped around a flexible pouch 12 for five different test animals. Each curve represents data from an individual animal experiment. As illustrated by the figure, the flow of blood through capillaries of muscle 40 is inversely dependent on the difference between arterial pressure of the skeletal muscle and the internal pouch pressure There is essentially no flow of blood through capillaries of muscle 40 during the muscle contraction phase, and only a limited flow of blood through the capillaries during the pouch filling phase. Accordingly, muscle fatigue associated with the low blood flow levels is minimized in accordance with this invention by keeping valve 24 closed during each cycle of operation for as long as possible without detracting from the efficient blood pumping action of the cardiac assist device. The interval of time that valve 24 can remain closed in each cycle of device operation is limited by the cycle time and the pumping requirements of the cardiac assist device 10.

For effective pumping action, the pouch filling phase must be of sufficient duration to allow the flexible pouch 12 to be filled with a sufficient volume of blood so that its expulsion from flexible pouch 12 by contraction of muscle 40 works to supplement the pumping action of the heart 20. An important function of the pouch filling phase is to adequately stretch muscle 40 surrounding the reservoir 12 so that maximal contractile force can be generated. Skeletal muscle such as rectus abdominis muscle 40 follows Starling's Law, which states that an increase in the stretch of the relaxed muscle fibers acts to increase the force of contraction, up to a finite limit. To maximize the compressive forces applied by muscle 40 upon contraction, its muscle fibers must be stretched during the pouch filling phase. Generally, the contractile force of the rectus abdominis 40 is optimized when the pressure within flexible pouch 12 reaches about 60-100 millimeters of Hg. The valve open time (VOT) determines this stretching pressure. Achieving this optimal blood pressure is generally feasible because even a heart in end-stage failure can generate 60-80 millimeters of Hg pressure in its left ventricle during contraction.

The pouch filling phase is initiated as valve 24 is opened in response to an electrical signal from pulse generator 28 to solenoid 26. Blood from aorta 18 is admitted into flexible pouch 12 through blood inlet conduit 14. The pressure within flexible pouch 12 increases as it fills with blood, and as the pressure exerted by the flexible pouch 12 against the muscle 40 surrounding flexible pouch 12 increases, the flow of blood through the cappillaries of muscle 40 is reduced. The pouch filling phase ends upon termination of the electrical signal activating solenoid 26 and closure of valve 24.

Subsequent to closure of valve 24, a muscle contracting stimulus is transmitted from the pulse generator 28 via the electrical leads 30, 32, 34, and 36 respectively to motor nerves 31, 33, 35, and 36 to cause contraction of the rectus abdominis muscle 40. The muscle contracting stimulus is generally in the form of a train of short duration electrical pulses that promote a smooth contraction of the rectus abdominis muscle 40. Blood contained within the flexible pouch 12 is expelled into aorta 18, supplementing the pumping action of the heart 20. Throughout the muscle contraction phase, the flow of blood through the capillaries of rectus abdominis muscle 40 is negligible. The inlet valve 24 remains closed following termination of the muscle contracting stimulus, and outlet valve 22 closes as the pressure within the flexible pouch 12 drops below the aortic blood pressure, thereby preventing backflow of blood into flexible pouch 12 and consequently maintaining low pouch pressure in flexible pouch 12.

Pulse generator 28 is programmed to repeat the above described 3-phase cycle in timed relationship with the activity of heart 20 as detected by heart sensor 50. Typically the cycled phases of cardiac assist device are coordinated with natural heart function in a counterpulsation mode so that contraction of the muscle 40 occurs during heart 20 diastole. Ideally, each cycle of heart action is supplemented by the blood pumping action of cardiac assist device 10. However device 10 can be used in other modes. For example the cardiac assist device 10 can be set to cycle once for every 2, 3 or more cycles of natural heart activity, or to alternatively operate independent of heart activity.

It should also be recognized that the assist device can be connected in other ways to a patients circulatory system. For example, it can be connected between the left ventricle and the aorta, between the left atrium and the aorta or receiving input from both the left atrium and left ventricle.

Figure 3:
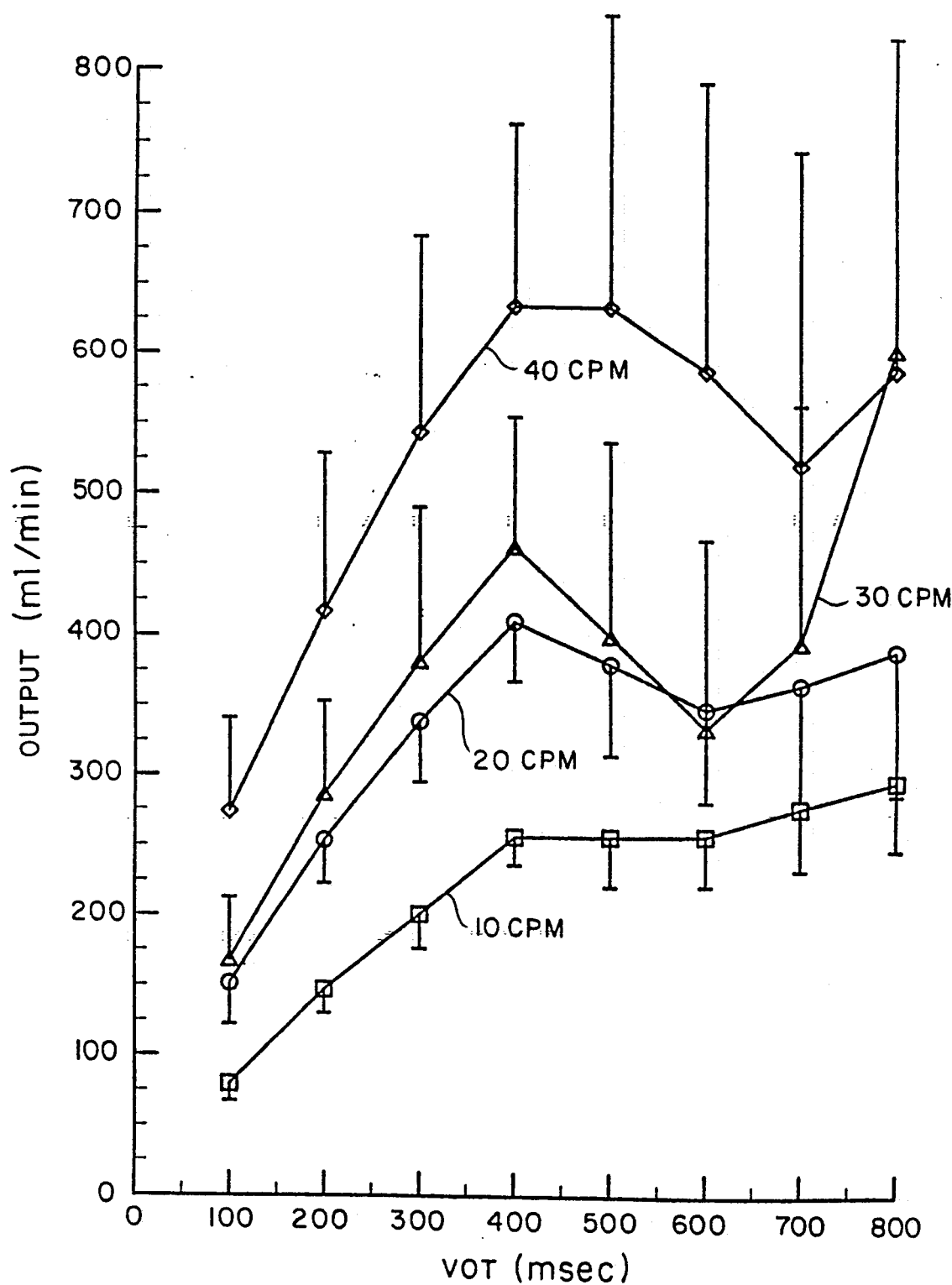
FIG. 3 is a graphic presentation of the output of a rectus abdominis powered cardiac assist device similar to that shown in FIG. 1 as a function of the valve open time (VOT) and train rate (contractions per minute; CPM)
Figure 4:
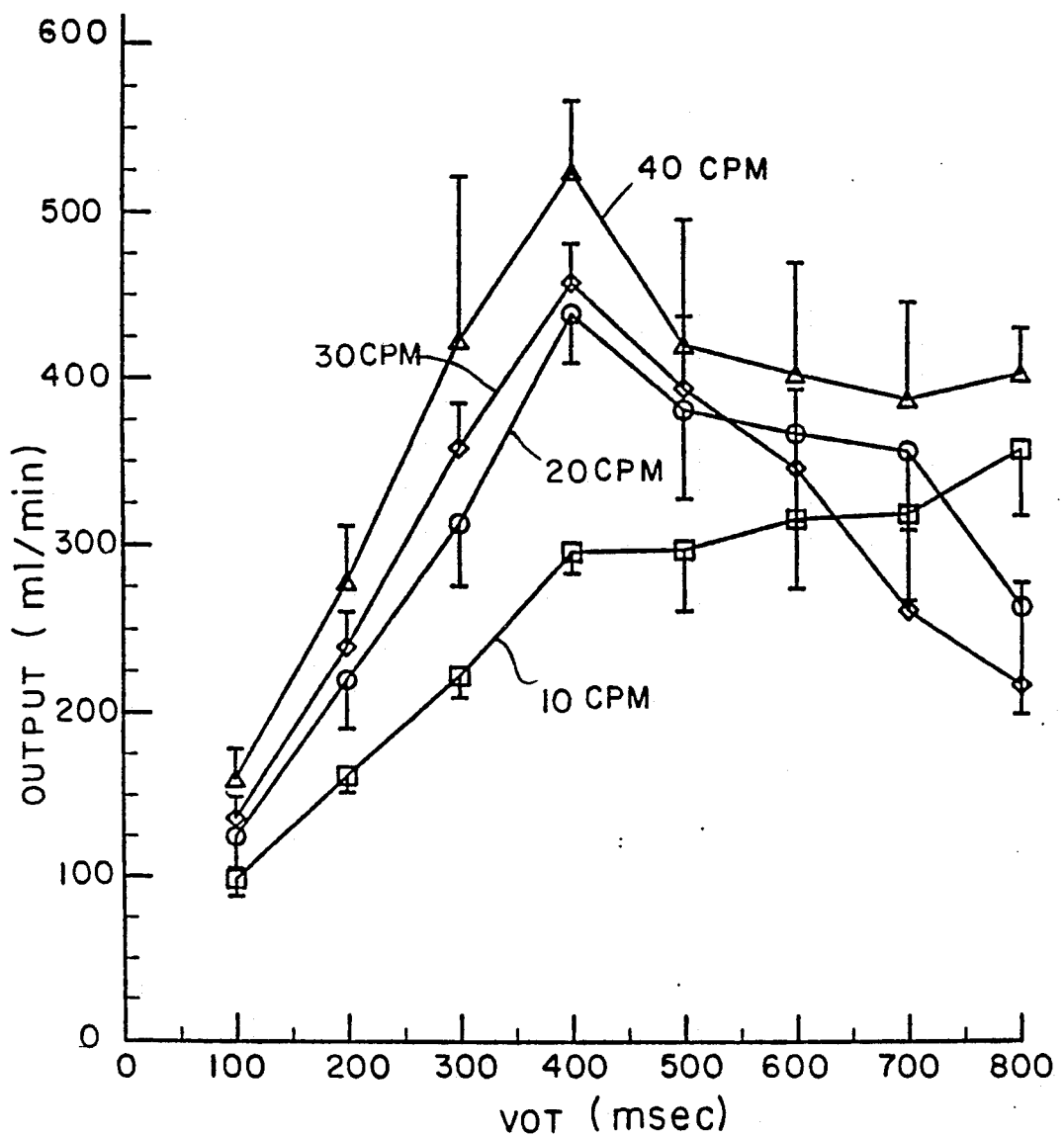
FIG. 4 is a graphic representation of the output of a latissimus dorsi powered cardiac assist device similar to that shown in FIG. 1 as a function of the valve open time (VOT) and train rate (contractions per minute; CPM)

The stroke output of the cardiac assist device 10 in accordance with this invention critically depends upon the interval of time that the inlet valve 24 remains open during each operational cycle of the device. If the valve open time (VOT) is too short, it will not allow flexible pouch 12 time to fill with enough blood to optimally preload muscle 40. Further, inadequate filling time simply will not allow enough blood into the device to supplement the blood pumping action of the heart 20. Extending the valve open time excessively on the other hand decreases the duration of the muscle perfusion phase. If the valve open time is too long, muscle fatigue becomes a problem. FIGS. 3 and 4 respectively illustrate the blood pumping output in milliliters/minute as a function of VOT for a rectus abdominus muscle and a latissimus dorsi muscle contracted at four different train rates (10, 20, 30, and 40 contractions per minute; CPM) used in a cardiac assist device similar to that illustrated in FIG. 1. As indicated by the graph, stroke output increases as VOT is increased from 100 to about 400 milliseconds. For each of the devices tested there exists an optimal valve open time of about 400 milliseconds. Optimum VOT can be expected to vary with inlet filling pressure, flexible pouch volume, its compliance and the pumping rate, ie. number of contractions per minute.

The length of time that the muscle contracting stimulus is repeatedly applied to the muscle during each cycle of cardiac assist device operation is referred to as the pulse train duration (PTD). Pulse train duration is an important parameter that should be optimized for efficient operation of a cardiac assist device in accordance with this invention. If the PTD is too short, the blood reservoir will not be sufficiently compressed to expel the volume of blood necessary to adequately supplement the blood pumping action of the heart 20. However, increasing the pulse train duration decreases the time available for the muscle perfusion phase The PTD need only be long enough for the velocity of blood flow from the flexible pouch to approach zero. Further, long PTD's can physically damage muscle cells and is wasteful of muscle energy.

Figure 5:
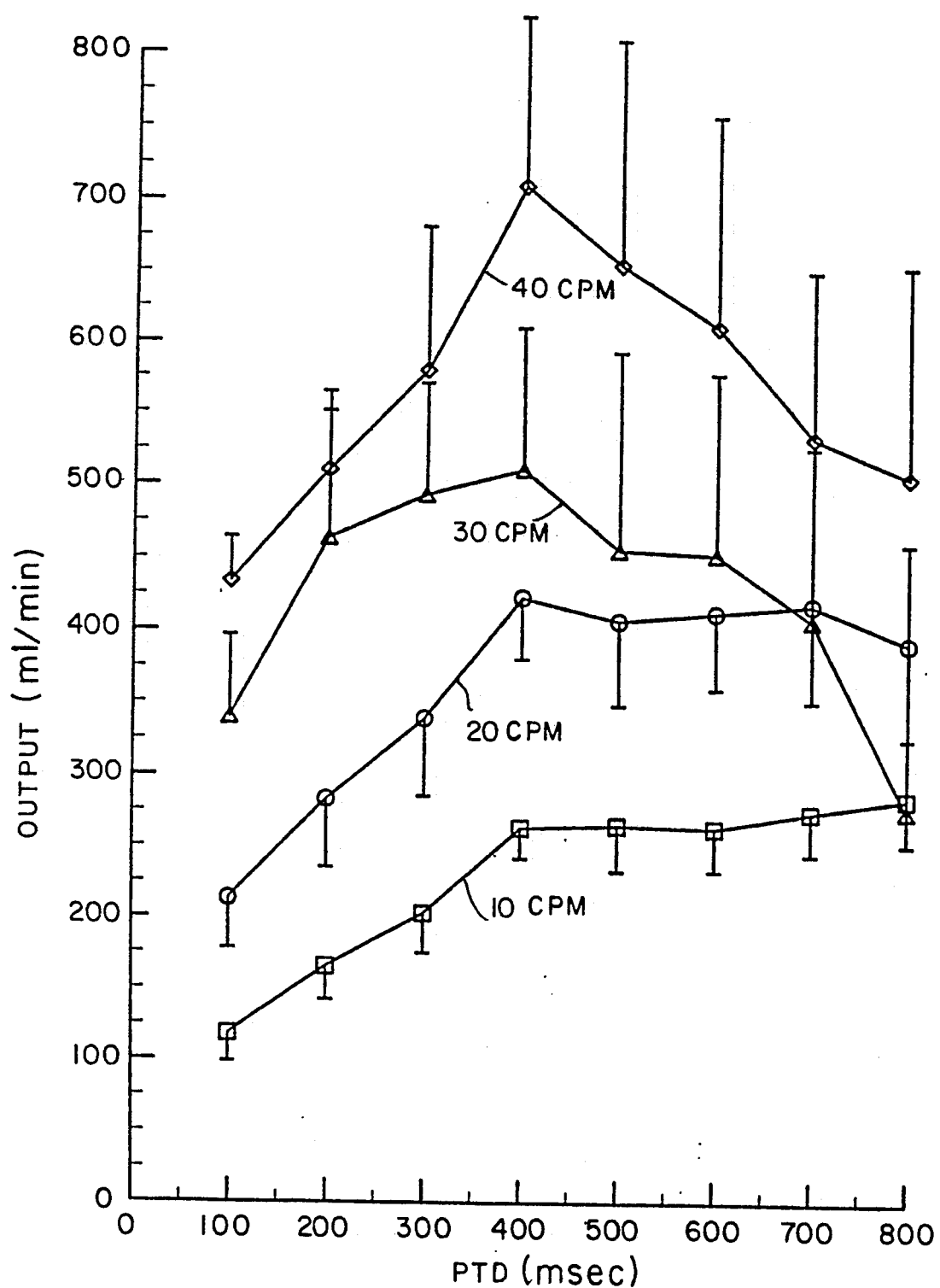
FIG. 5 is a graph showing the output of a rectus abdominis powered blood pump similar to that shown in FIG. 1 as a function of the pulse train duration (PTD) and train rate (contractions per minute; CPM)
Figure 6:
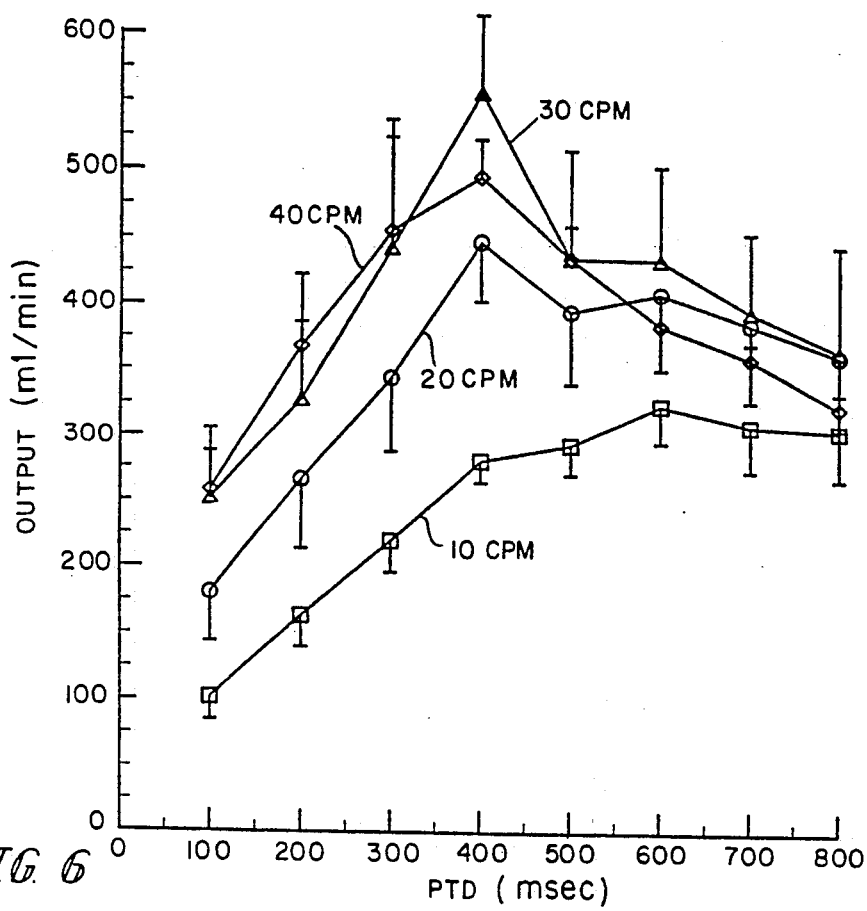
FIG. 6 is a graphic representation of the output of a latissimus dorsi powered cardiac assist device similar to that shown in FIG. 1 as a function of the pulse train duration (PTD) and train rate (contractions per minute; CPM)

FIGS. 5 and 6 respectively illustrate the blood pumping output in milliliters/minute for a rectus abdominis muscle and a latissimus dorsi muscle contracted at four different train rates (10, 20, 30, and 40 contractions per minute; CPM) used in a cardiac assist device similar to that illustrated in FIG. 1. As indicated by the graph, there exists an optimal pulse train duration of about 400 milliseconds for the particular cardiac assist device used. A PTD shorter than optimal will not maximize device output and a longer than optimal PTD will not provide for any increase (and may even decrease) the device output while severely compromising muscle blood capillary flow. As with the valve open time, the optimal PTD will depend on many factors such as pouch volume, pouch filling pressure, type of interface with the circulatory system, magnitude of compressive forces, valve open time, and coordination of device operation with heart activity.

In addition to PTD another aspect of the muscle contracting stimulus from the pulse generator 28 is the type of electrical signal transmitted to the skeletal muscle 40 powering the cardiac assist device 10. A single electrical pulse delivered to a motor nerve of a skeletal muscle can result in a twitch contraction of the skeletal muscle. Alternatively, repetition of the electrical pulses at a just sufficiently high frequency can result in a fused contraction of the skeletal muscle that is characterized as a tetanic contraction that is much more forceful than the twitch. It has been found that a train of pulses having the lowest frequency that will reliably produce a smooth tetanic contraction provides greater contractile force than twitch stimuli. When frequency is too low, not only is contractile force less, but muscle capillary flow decreases secondary to increased pouch diastolic pressure. The pulses can be in the form of either a standard square wave, capacitor discharge or induction coil shock, or a ramped pulse that may help to promote the conversion of fast twitch muscle fibers into the more preferred slow twitch muscle fibers. The use of higher frequency pulses is unnecessary and can create unwanted neuromuscular fatigue.

Following implantation of the cardiac assist device a muscle training regimen can be implemented to promote conversion of fast twitch muscle fibers into slow twitch muscle fibers. This training regimen generally includes the application of a series of electrical pulses to cause muscle twitching and a higher frequency train of electrical pulses to cause tetanic muscle contraction. It has been found that conversion of fast twitch muscle fibers into slow twitch muscle fibers is promoted when the muscle contracting stimulus alternates between pulses that cause twitch contraction and the frequency of pulses that cause tetanic contraction. That regimen has the advantage of permitting concurrent blood pumping action during the training period. Conversion of fast twitch muscle fibers into less easily fatigued slow twitch muscle fibers is essentially complete after a six week training regimen.

The following examples are presented to further illustrate use and operation of the present invention.

EXAMPLE 1

Five healthy mongrel dogs were anesthetized with pentobarbital sodium (30 mg/kg, iv), intubated, and placed in either dorsal or right-lateral recumbency upon a heating pad. A surgical plane of anesthesia was maintained by administering additional pentobarbital (60–90 mg, iv) as needed. A catheter was placed in the femoral vein for the administration of drugs or fluids.

Figure 8:
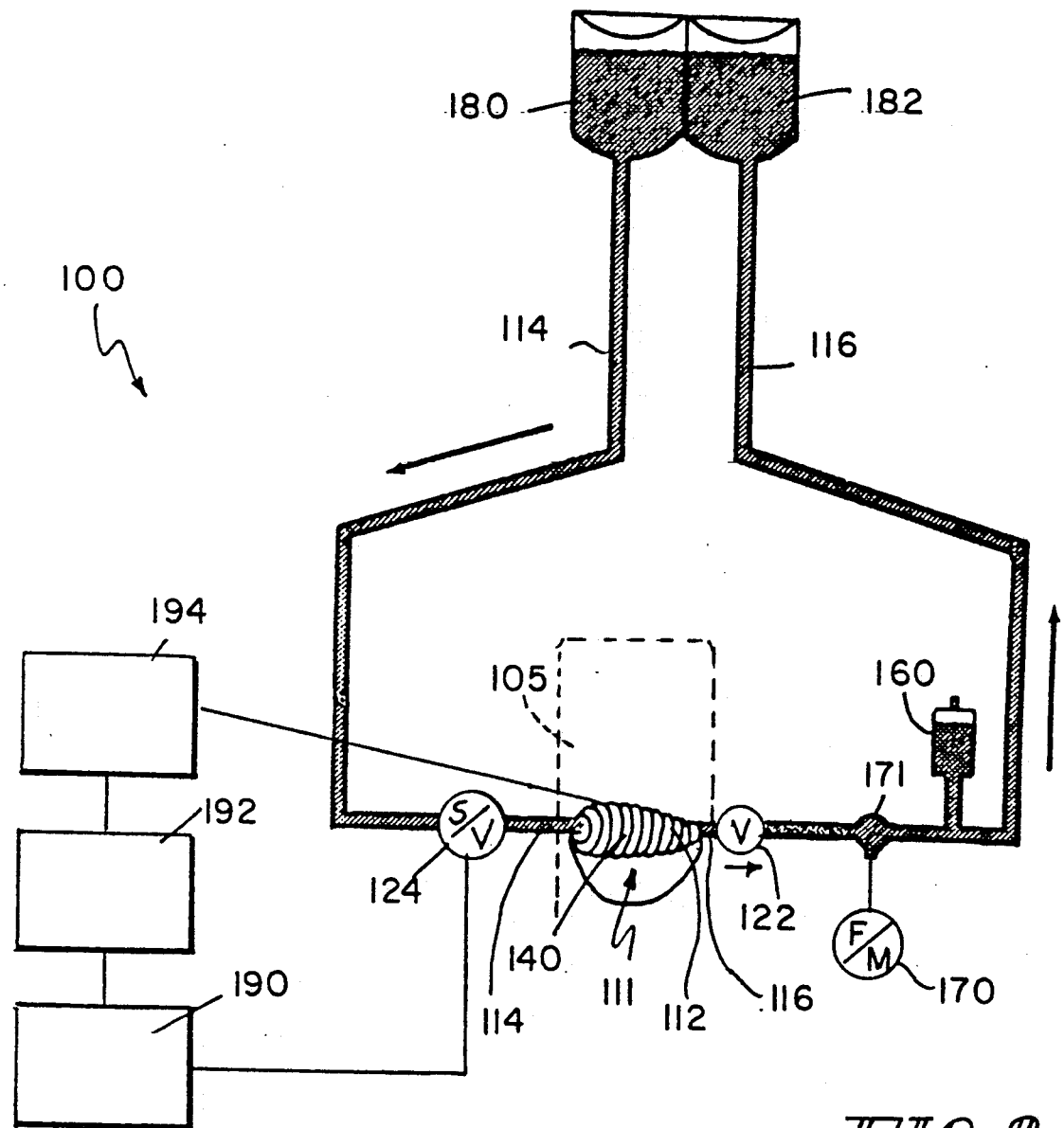
FIG. 8 is a schematic illustration of a mock circulation apparatus used to test canine skeletal muscle ventricles.

FIG. 8 illustrates a mock circulation apparatus 100 devised to evaluate the pumping capabilities of a skeletal muscle ventricle 111. The skeletal muscle ventricle 111 included a left rectus abdominus muscle 140 is maintained in neurovascular connection with dog 105 throughout the experiment. The muscle 140 is translocated and wrapped around a flexible pouch 112 so that muscle 140 compressed the pouch 112 when subjected to a muscle contracting stimulus. Saline contained in the flexible pouch 112 was pumped out of the flexible pouch 112 by the compressive forces exerted by the contracting rectus abdominis muscle 140 against an afterload pressure of 100 mm Hg achieved by setting the level of fluid in reservoir 182 at 136 centimeters above the level of the flexible pouch 112.

The left rectus abdominus muscle 140 was translocated using the following method: To provide exposure of the left rectus abdominis muscle 140, a midline skin incision was made from the ventral midthorax to just caudal to the umbilicus of the dog 105. A skin flap was formed over the left rectus abdominis muscle 140 until the medial margin of the external oblique attachments were identified. The rectus muscle 140 was dissected free of its attachments to the fascial sheath, transected just below the umbilicus, and its aponeurotic origin was divided. Because the anterior portion of the muscle is supplied by the inferior intercostal nerves, care was taken to preserve the five or six branches that supplied the muscle belly. The cranial epigastric blood vessels were also preserved, and the dissection was complete when the muscle remained attached to the body by only the intercostal nerves and the cranial epigastric blood supply. The rectus muscle 120 was then sutured into a conical shape in a spiral arrangement around an flexible pouch.

The flexible pouch 112 used in these studies was constructed from 11-cm wide (flattened width) polyethylene tubing (4 mil thickness). The ends of an approximately 10-cm long section of this tubing were fastened with purse-strong sutures and sealed with silastic to an inlet conduit 114 and an outlet conduit 116. The rectus abdominis muscle 140 was wrapped around the plastic pouch 112 so that unrestricted filling of the skeletal muscle ventricle 111 could occur. To accomodate the various canine muscles the resting volume of the muscle-wrapped pouch 112 ranged from 70 to 100 ml. The skeletal muscle ventricle 111 was kept moist and warm with saline-soaked gauze and a heating lamp (not shown). At the end of each experiment, the remaining attachments of the rectus abdominis were severed and the weight of the respective muscles was determined and recorded.

The skeletal muscle ventricle 111 was connected to an inlet reservoir 180 by an inlet conduit 114 and to a second reservoir by an outlet conduit 116. Both the inlet reservoir 180 and the outlet reservoir 182 contained saline. A passive single-flap valve 122 was positioned in the outlet conduit 116 and a solenoid valve 124 was connected between the first reservoir 180 and the flexible pouch 112. The solenoid valve 124 permitted the controlled filling of the flexible pouch 112 and unidirectional flow during contraction of the skeletal muscle ventricle 111. The preload and afterload pressures were set at 100 mmHg by adjusting the level of saline in the respective reservoirs 180 and 182.

To simulate the compliance of the aorta, a windkessel 160 was connected to the outlet conduit and consisted of a 250-ml inverted bottle filled with 190 ml of saline. An electromagnetic flowmeter 170 (Model 501, Carolina Medical Electronics, Inc., King, N.C.) and an inline flow probe 171 were connected to the outlet conduit 111 and used to measure the flow of saline during contraction of the rectus abdominis muscle 140 of the skeletal muscle ventricle 111. The stroke volume of the pouch 112 was obtained by electronically integrating the signal from the electromagnetic flow meter over time. Pouch outflow, pouch stroke volume, and pouch pressure were monitored using a graphic recorder (not shown).

Unipolar electrical stimulation of the inferior intercostal nerves (not shown in FIG. 8) was used to produce contraction of the rectus abdominis muscle 140. The exposed end of an insulated, multi-stranded length of wire (not shown) was inserted into the muscle immediately adjacent to each site of motor nerve entry; each end served as the cathode. The anode consisted of a metal clip applied to the medial edge of the abdominal skin incision.

To produce a tetanic contraction of the muscle, the motor nerves were stimulated with a train of 100 $\mu$sec current pulses at a frequency of either 40 or 50 per sec. This frequency range was selected to produce a smooth tetanic contraction that is optimal for operation of the skeletal muscle ventricle cardiac assist device. Stimulation current was supplied by a RF isolation unit connected to a first Grass stimulator 190 (Model S44, Grass Medical Instruments, Quincy, Mass.); its output was gated on and off by a second Grass stimulator 192. Therefore, the output of the second stimulator determined the duration of the train of stimuli. A third Grass stimulator 194 which determined the number of pulse trains/sec was used to trigger the stimulator that established the train rate. The pulse train duration could be varied from 100 to 1000 msec and the repetition rate of the train (i.e., the number of tetanic contractions/min of the skeletal muscle ventricle 111) could be varied from 1 to 50 min.$^{-1}$ In all experiments the output voltage applied to the electrodes was adjusted to ensure contraction of all muscle fibers.

The length of time the skeletal muscle ventricle 111 was exposed to the preload pressure was set by controlling the opening of the solenoid valve 124. This time (valve open time; VOT) was controlled by the third Grass stimulator 194 that established the train rate. A VOT range from 100–500 msec was available, but typically a VOT of 400 msec was used. Immediately after closure of the solenoid valve 124, the train of pulses acting to reliably trigger muscle contraction was delivered to the motor nerves.

By using the solenoid valve 124, the diastolic pressure of the flexible pouch 112 could be kept at a very low value, generally less than 20 millimeters of Hg, thereby allowing free blood flow through the muscle capillaries. When the solenoid valve 124 opened, the 100 mm Hg preload pressure caused saline to enter the pouch 112 and develop the precontraction pressure exerted against the muscle 140. In this way a high transient precontraction pressure on the muscle 140 was achieved to promote a strong contraction of muscle 140 without compromising blood flow to the muscle 140 during at least part of the skeletal muscle ventricle 111 diastolic period.

The skeletal muscle ventricle 111 was electrically stimulated to contract at a rate of either 10, 20, 30 or 40 min$^{-1}$. The pulse train duration (PTD) was typically set at 100 msec then increased in increments of 100 msec until a PTD of 800 msec was reached. The length of stimulation time using each PTD was approximately 30 sec. After the entire range of PTDs was tested at a given train rate, the stimulation procedure was repeated for different train rates until rates of 10, 20, 30, and 40 min$^{-1}$ were all tested. The sequence of train rates was chosen randomly for each animal to minimize the effect of fatigue upon the results from the stimulation procedures that were performed near the end of the experiment. Stated differently, one skeletal muscle ventricle 111 may have been tested at a train rate of 10 first, then 20, 30 and finally 40 min,$^{-1}$ and the next skeletal muscle ventricle 111 may have been tested at a rate of 40 first, then 20, 30 and finally 10 min.$^{-1}$ During the rest periods between stimulation at different train rates, the skeletal muscle ventricle 111 pouch was manually emptied so that the enveloping muscle was not exposed to a resting intraluminal pressure that could compromise muscle blood flow. To determine if muscle fatigue was occurring during the course of the experiment, the stimulation procedure was repeated at the PTD which showed the greatest stroke volume after the entire sequence of PTDs was tested for each contraction rate. If there was greater than 20% difference in the measured stroke volume during this repeat procedure, then the difference was attributed to fatigue and not to the electrical stimulation protocol.

The maximum flow output as measured by the flowmeters 170 and 171 was obtained when a PTD of 400 msec ($p < 0.01$ when compared to values for PTDs at 100, 200, or 300 msec) was used for contraction rates of 20, 30, and 40 min.$^{-1}$ When the skeletal muscle ventricle 111 was stimulated to contract at a rate of 10 min$^{-1}$ the optimal PTD was 800 msec, but the output was only marginally greater than that at a PTD of 400 msec (FIG. 2).

Comparison of skeletal muscle ventricle 111 output among the 4 train rates for a given PTD showed that output nearly always increased as the train rate was increased. The highest mean skeletal muscle ventricle 111 output recorded in this study for dogs with a rectus abdominis skeletal muscle ventricle 111 was 710 ml min$^{-1}$ when the train rate was 40 min$^{-1}$ and the PTD was 400 msec. The greatest skeletal muscle ventricle 111 output for train rates of 30, 20, and 10 min$^{-1}$ were 511, 423, and 285 ml/min, respectively.

EXAMPLE 2

The procedure followed to construct a cardiac assist device using a latissimus dorsi muscle in this example corresponds to the procedure outlined in Example 1, with the following exceptions:

For the 5 dogs in which the latissimus dorsi muscle was used to construct the skeletal muscle ventricle, a dorsal midline incision and two lateral incisions were made along the thoracic wall to form a skin flap that provided exposure of the muscle. The latissimus muscle was dissected free of its attachments to fascial sheaths, and the muscle was transected along its caudal and medial margins. The muscle remained attached to the body at its insertion to the humerus where the thoracodorsal nerve, artery and vein were carefully preserved. The latissimus muscle was then sutured into a cylindrical shape in a circumferential arrangement around a compressible flexible pouch.

Bipolar stimulation of the thoracodorsal nerve was employed to produce contraction of the latissimus dorsi muscle. Following dissection of the latissimus muscle, the brachial plexus was exposed through a skin incision in the left axilla. A hand-held bipolar stimulator was applied intermittently to the plexus to aid in identification and isolation of the thoracodorsal nerve. A bipolar sleeve electrode was then secured around the nerve.

The maximum output for a latissimus dorsi skeletal muscle ventricle was obtained when a PTD of 400 msec was used for train rates of 20, 30, and 40 min.$^{-1}$ When the skeletal muscle ventricle was stimulated with a train rate of 10 min,$^{-1}$ the maximum output was obtained with a PTD of 600 msec, but the output was very similar for all PTDs from 400 through 800 msec (FIG. 3). The skeletal muscle ventricle outputs at a PTD of 400 msec for each trainrate were significantly greater ($p < 0.01$) than the respective outputs at 100, 200, and 300 msec PTDs.

Just as with the rectus abdominis skeletal muscle ventricle 111, the latissimis dorsi skeletal muscle ventricle output for a given PTD usually increased as the train rate increased. The highest mean skeletal muscle ventricle output recorded for dogs with a latissimu dorsi skeletal muscle ventricle was 556 ml min$^{-1}$ when the train rate was 30 min$^{-1}$ and the PTD was 400 msec. The greatest skeletal muscle ventricle output for train rates of 40, 20 and 10 min$^{-1}$ were 495 ml, 448 ml, and 323 ml, respectively.

EXAMPLE 3

Twelve dogs (21–32 kg) were randomly assigned to 3 groups of 4 each. A compressible, fluid-filled pouch was placed between the latissimus dorsi muscle and the chest wall of each dog. The pouch was connected to an implanted venturi flowmeter with accessible subcutaneous pressure ports that permitted measurement of fluid flow through the system as the muscle contracted and compressed the pouch. The fluid passing through the flowmeter entered a subcutaneous, low compliance chamber. The motor nerve to the muscle was stimulated by a wearable induction stimulator, programmed for one of three different electrical stimulation regimens. The stimulation period continued for 6 consecutive weeks. The effect of these different stimulation regimens upon muscle function (i.e., flow generating ability and fatigue resistance) was determined at weekly intervals. A biopsy specimen was obtained from both the right and left latissimus dorsi muscle of each dog before the beginning of electrical stimulation and at the end of week 6 to determine the extent of muscle fiber transformation. A comparison of latissimus dorsi muscle structure and function between the 3 groups was made at the end of week 6.

Each animal was anesthetized with pentothal sodium (20 mg/kg I.V.), then intubated and a surgical plane of anesthesia was maintained with 1.5% Halothane and oxygen. A vertical incision was made over the ninth rib to expose the right latissimus dorsi muscle. The muscle was dissected free of its attachments to the subcutaneous tissue and to the underlying ribs in the region of the muscle belly. The origin and insertion of the muscle and the neurovascular supply remained intact. An oblong, compressible pouch with a volume of approximately 70 ml at 30 mmHg pressure and coated with the silastic 236 polymer (Dow Corning, Midland, Mich.) was placed between the muscle belly and the chest wall. The pouch was connected to the venturi flowmeter, which in turn was fitted with 2 accessible subcutaneous pressure ports. The flowmeter was connected to a low compliance chamber. Two mobile pressure ports were placed in the subcutaneous tissue near the thoracic dorsal spinous processes. The combination of a compressible compliant pouch and an attached low compliance chamber provided a preload against which the stimulated muscle could work in an isotonic contraction mode. When the muscle relaxed, recoil of the low compliance chamber refilled the pouch beneath the muscle belly. The system was filled with sterile saline to provide a preload of 30 mm Hg for the latissimus dorsi muscle to contract against.

The second incision was made in the right axillary region caudal to the deep pectoral muscle to isolate the thoracodorsal motor nerve, and a bipolar cuffed electrode was applied to this nerve as it coursed toward the latissimus dorsi muscle. To eliminate the infection problems that frequently plague electrical stimulators that employ transcutaneous leads, a passive implantable stimulator consisting of a 300-turn stainless-steel coil that received the transmitted stimuli from a second coil placed over it on the skin surface was used. The ends of the implanted coil served as the electrodes on the motor nerve. A pulsed magnetic field provided by the skin-surface excitation coil induced a voltage in the implanted coil. Use of this method allowed easy external control of the electrical stimulation frequency and intensity.

The external stimulator was connected to a skin-surface excitation coil residing in a small back pack that allowed total freedom of movement for the dogs. The stimulus waveform was a short-duration (0.1 msec) damped sinusoid, which provided satisfactory stimulation of the motor nerve. After coil implantation, all the dogs were given a 3-day recovery period before the electrical stimulation regimens were started.

Three different electrical stimulation regimens were used, one for each group of 4 dogs. Group 1 received continuous, 2 $\sec^{-1}$, single impulse stimulations which caused twitch muscle contractions. This regimen is similar to that used by other investigators to produce conversion to type I fatigue-resistant fibers. Group 2 received trains of stimuli at a frequency of 36 $\sec^{-1}$ and lasting 250 msec (i.e., 9 stimuli per pulse train) at a rate of 30 pulse trains $\min^{-1}$ for 15 min, followed by 15 min of no stimulation. This exercise-rest cycle was repeated continuously. Thus, dogs in group 2 received a regimen of intermittent tetanic contractions with regular rest periods. Group 3 received both twitch and tetanic stimulation during alternate 15 min periods without any rest periods.

The flow (Q) through the venturi flowmeter depended on the square root of the pressure difference $(P_1 - P_2)$ between the two specified positions on the venturi tube. This pressure difference was measured via the subcutaneous access ports and flow was determined by the following equation:

$$Q = k (P_1 - P_2)^{\frac{1}{2}}$$

where k is a constant that was determined experimentally for each flowmeter prior to implantation.

An electromagnetic flow-through flowmeter (30 mm I.D., Carolina Medical Instruments, King, N.C.) was used for calibration and was placed between the distal end of the venturi flowmeter and the low-compliance chamber. Flow was recorded when the pouch was compressed manually. Release of the compression permitted recoil of the less compliant chamber and reverse flow then occurred which refilled the pouch. The pressure difference produced at the two ports was recorded by inserting 20 gauge needles into the access ports and using a differential pressure transducer. Data were recorded on a Physiograph recorder (Narco Bio Systems, Houston, Tex.). The square root of the pressure difference was plotted versus flow as measured by the electromagnetic flowmeter. Calibration of each device was performed both before implantation and after explanation from the dogs to verify constancy of calibration.

Once each week, the dogs were anesthetized with intravenous pentothal sodium (20 mg/kg) and an evaluation was made of the flow produced by muscle contraction and its change (i.e., reduction) with time. Muscle fatigue was defined as a 50% decrease in flow $\min^{-1}$ through the venturi flowmeter with stimulation parameters unchanged. To make valid comparisons for the three regimens, it was important to standardize the stimulation protocol during each fatigue trail. A Grass stimulator was used to deliver pulses to the back-pack unit which transmitted the stimuli to the implanted coil receiver connected to the motor nerve of the latissimus dorsi muscle. The electrical stimulation used to cause fatigue was characterized by a pulse frequency of 40 $\sec^{-1}$ (to cause tetanic muscle contractions), a pulse train duration of 250 msec, and a stimulation rate of 60 $\min^{-1}$. Prior to the beginning of data collection, the stimulus current was increased until all of the motor nerve fibers were excited, evidenced by no further increase in flow. The baseline flow for each dog was established by measuring flow during the first 30 seconds of electrically stimulated muscle contraction. Flow was then measured and summed for every 30 seconds thereafter during contraction until a flow value of 50% of the baseline flow was reached.

At the time of the original surgery, a 1.0 cm (width) × 2.0 cm (length) full thickness biopsy specimen was taken from the middle of the muscle belly of both the right and left latissimus dorsi muscles. Metal clamps were used when collecting the specimens to prevent contraction after excision but before fixation. The specimens were quickly frozen in isopentane, placed in an air tight plastic pouch, and then immersed in liquid nitrogen for storage. A second biopsy specimen was taken adjacent to the original biopsy site in the muscles of each dog after the 6-week electrical stimulation period. All specimens were stored at $-70°$ C. until the time of histochemical processing (i.e., within 2 days). Serial transverse frozen sections, 7 $\mu$m thick, were cut on a cryostat and stained for myofibrillar adenosine triphosphatase (ATPase) with both an acid (pH 4.4) and an alkaline (pH 10.4) preincubation (9).

All dogs tolerated the back-packs very well. After 1 to 2 days of electrical stimulation, the dogs appeared to be unaware of the muscle stimulation. The calibration tests for each flowmeter showed no measurable difference between the values recorded before implantation and those recorded after explantation. The results of the weekly muscle fatigue testing showed that Regimen 1 (continuous 2 $sec^{-1}$ twitch stimulation) caused a significant increase in fatigue resistance, from 9 to 116 min ($p < 0.001$), but a decrease in pumping ability, expressed in terms of minute flow, from 0.25 to 0.14 L $min^{-1}$ ($p < 0.05$) over the 6-week period. Regimen 2 (alternating 15 min periods tetanic stimulation and rest), caused neither a significant change in fatigue resistance (from 7 to 11 min; p=NS), nor a change in minute flow from 0.21 to 0.20 L $min^{-1}$ (p=NS), over the 6 week period. Regimen 3 (alternating periods of twitch and tetanic contractions) caused a significant increase in fatigue resistance, from 9 to 107 min ($p<0.001$) and a negligible change in minute flow from 0.20 to 0.22 L $min^{-1}$ (p=NS). The preferred training regimen to promote conversion of fast twitch into slow twitch muscle fibers was therefore determined to be Regimen 3.

We claim:

1. An apparatus for enhancing circulation of blood in skeletal muscle in use for powering a cardiac assist device including a blood reservoir in fluid communication with a patient's circulatory system, wherein said skeletal muscle is positioned to compress the blood reservoir in response to a muscle contracting stimulus from a pulse generator said circulation enhancing apparatus comprising a valve positioned to control blood flow from the patient's circulatory system into the blood reservoir, and means for activating the valve in a timed relationship to the muscle contracting stimulus.

2. The apparatus of claim 1 wherein the valve activating means is a programmable signal generating circuit in the pulse generator.

3. The apparatus of claim 1, wherein the blood reservoir has a blood outlet conduit and a blood inlet conduit each in fluid communication with the patient's circulatory system, and wherein the valve is positioned in the blood inlet conduit and a unidirectional valve is positioned in the blood outlet conduit to prevent blood flow from the patient's circulatory system into the blood reservoir through said blood outlet conduit.

4. The apparatus of claim 1 wherein the valve is biased in a closed position.

5. The apparatus of claim 4 wherein the valve is electrically activated by an electric pulse generator in an adjustable timed relationship to the muscle contracting stimulus.

6. The apparatus of claim 1 further comprising means for sensing heart activity wherein the muscle contracting stimulus from the pulse generator is applied to the skeletal muscle in a timed relationship to sensed heart activity.

7. An apparatus for enhancing circulation of blood through skeletal muscle in use for powering a cardiac assist device for providing blood pumping action to supplement heart blood pumping action, wherein said skeletal muscle is positioned to compress a blood reservoir in response to a muscle contracting stimulus, the blood reservoir in fluid communication with a patient's circulatory system, said apparatus comprising, a blood outlet conduit and a blood inlet conduit, each in fluid communication with the patient's circulatory system and the blood reservoir, an unidirectional flow valve in the blood outlet conduit to prevent blood flow from the patient's circulatory system into the blood reservoir through the blood outlet, an electrically activated valve positioned in the blood inlet conduit to control blood flow from the patient's circulatory system into the blood reservoir, and means for activating the electrically activated valve in a timed relationship to the muscle contracting stimulus.

8. A method for enhancing circulation of blood through skeletal muscle used for powering a cardiac assist device including a blood reservoir in fluid communication with a patient's circulatory system in which device said skeletal muscle is positioned to compress the blood reservoir in response to muscle contracting stimuli, said method comprising the step of delaying blood flow into the blood reservoir for a predetermined period of time following each muscle contracting stimulus.

* * * * *

UNITED STATES PATENT AND TRADEMARK OFFICE
CERTIFICATE OF CORRECTION

PATENT NO. : 5,007,927
DATED : April 16, 1991
INVENTOR(S) : Stephen F. Badylak; Leslie A. Geddes; Jerry L. Wessale It is certified that error appears in the above-identified patent and that said Letters Patent is hereby corrected as shown below:

In Column 1, Line 4 before "FIELD OF THE INVENTION", please insert the following paragraph:

--This invention was made with Government support under Grant Number HL 39724 awarded by the National Institute of Health. The Government has certain rights in the invention.--

Signed and Sealed this

Twenty-first Day of December, 1993

*Attest:*

BRUCE LEHMAN

*Attesting Officer*     *Commissioner of Patents and Trademarks*